(12) United States Patent
Vinayagamoorthy

(10) Patent No.: US 10,036,053 B2
(45) Date of Patent: *Jul. 31, 2018

(54) DETERMINATION OF VARIANTS PRODUCED UPON REPLICATION OR TRANSCRIPTION OF NUCLEIC ACID SEQUENCES

(71) Applicant: Bio-ID Diagnostic Inc., Edmonton (CA)

(72) Inventor: Thuraiayah Vinayagamoorthy, Charlotte, NC (US)

(73) Assignee: Bio-ID Diagnostics Inc., Edmonton, AB (CA)

( * ) Notice: Subject to any disclaimer, the term of this patent is extended or adjusted under 35 U.S.C. 154(b) by 183 days.

This patent is subject to a terminal disclaimer.

(21) Appl. No.: 14/869,914

(22) Filed: Sep. 29, 2015

(65) Prior Publication Data

US 2016/0138083 A1    May 19, 2016

Related U.S. Application Data

(63) Continuation of application No. 11/475,921, filed on Jun. 28, 2006, now Pat. No. 9,150,906.

(51) Int. Cl.
*C12P 19/34* (2006.01)
*C12Q 1/6806* (2018.01)
*C12Q 1/6813* (2018.01)

(52) U.S. Cl.
CPC ......... *C12Q 1/6806* (2013.01); *C12Q 1/6813* (2013.01)

(58) Field of Classification Search
USPC .............................. 435/6.12, 91.2
See application file for complete search history.

(56) References Cited

U.S. PATENT DOCUMENTS

| 4,683,195 A | 7/1987 | Mullis et al. |
| 4,683,202 A | 7/1987 | Mullis et al. |

(Continued)

FOREIGN PATENT DOCUMENTS

| EP | 0 318 341 | 5/1989 |
| EP | 0 208 418 | 12/1998 |

(Continued)

OTHER PUBLICATIONS

"Gene Structure" Guide to the Human Genome (2010) pp. 1-8.
(Continued)

*Primary Examiner* — Kenneth R Horlick

(57) ABSTRACT

A method of determining whether or not a nucleic acid having an expected sequence or one or more variants of the expected sequence are present in a sample containing nucleic acids after replication, transcription or editing (or other transformation) of a substrate nucleic acid. The method involves deciding an expected sequence likely to be formed in the sample upon the replication, transcription or editing of the substrate nucleic acid, and possible variants of the expected sequence, providing primer pairs for a polymerase chain reaction, reverse transcriptase polymerase chain reaction or ligase chain reaction, carrying out the polymerase chain reaction or reverse transcriptase polymerase chain reaction in one or more steps to form amplicons, and analyzing the amplicons to determining whether or not a nucleic acid having the expected sequence and/or variants are present in the sample. The primers of the primer pairs are designed to anneal to regions of the nucleic acid of the expected sequence and the variants, the regions being selected to reveal unambiguously the presence or absence in the sample of the nucleic acid of the expected sequence or the variants thereof according to the presence or absence of specific amplicons amplified by the primers.

6 Claims, 8 Drawing Sheets

(56) References Cited

U.S. PATENT DOCUMENTS

| | | | |
|---|---|---|---|
| 4,775,619 | A | 10/1988 | Urdea et al. |
| 4,851,331 | A | 7/1989 | Vary et al. |
| 4,965,188 | A | 10/1990 | Mullis et al. |
| 5,227,292 | A | 7/1993 | White et al. |
| 5,376,355 | A | 12/1994 | Turteltaub et al. |
| 5,403,707 | A | 4/1995 | Atwood et al. |
| 5,552,283 | A | 9/1996 | Diamandis et al. |
| 5,582,989 | A | 12/1996 | Caskey et al. |
| 5,622,824 | A | 4/1997 | Koster et al. |
| 5,661,028 | A | 8/1997 | Foote et al. |
| 5,711,310 | A | 1/1998 | Vinayagamoorthy et al. |
| 5,776,737 | A | 7/1998 | Dunn et al. |
| 5,912,129 | A | 6/1999 | Vinayagamoorthy et al. |
| 5,994,528 | A | 11/1999 | Vinayagamoorthy et al. |
| 6,010,908 | A | 1/2000 | Gruenert et al. |
| 6,140,110 | A | 10/2000 | Vinayagamoorthy et al. |
| 6,197,510 | B1 | 3/2001 | Vinayagamoorthy et al. |
| 6,998,473 | B1 | 2/2006 | Crofts et al. |
| 7,691,614 | B2 | 4/2010 | Senapathy et al. |
| 2003/0165868 | A1 | 9/2003 | Lacroix et al. |
| 2004/0219565 | A1 | 11/2004 | Kauppinen et al. |
| 2007/0072212 | A1 | 3/2007 | Vinayagamoorthy et al. |
| 2008/0118915 | A1 | 5/2008 | Vinayagamoorthy et al. |

FOREIGN PATENT DOCUMENTS

| | | |
|---|---|---|
| WO | WO-1991/04270 | 4/1991 |
| WO | WO-1991/13993 | 9/1991 |
| WO | WO-1991/19816 | 12/1991 |
| WO | WO-1993/06243 | 4/1993 |
| WO | WO-1994/10315 | 5/1994 |
| WO | WO-1994/021822 | 9/1994 |
| WO | WO-1995/011294 | 4/1995 |
| WO | WO-1997/043441 | 11/1997 |
| WO | WO-1998/026095 | 6/1998 |
| WO | WO-1999/029900 | 6/1999 |
| WO | WO-2000/020628 | 4/2000 |
| WO | WO-2007/095723 | 8/2007 |

OTHER PUBLICATIONS

Abu Al-Soud et al., "Effects of amplification facilitators on diagnostic PCR in the presence of blood, feces, and meat," J Clin Microbiol (2000) 38(12):4463-4470.

Akduman et al., "Evaluation of a strand displacement amplification assay (BD ProbeTecSDA) for detection of Neisseria gonorrhea in urine specimens," J Clin Microbiol (2002) 40:281-283.

Betsou et al., "Construction and evaluation of internal control Nucleic Acids for PCR amplification of Chlamydia trachomatis Nucleic Acids from urine samples," J Clin Microbiol (2003) 41:1274-1276.

Bourdon et al., "P53 isoforms can regulate p53 transcriptional activity," Genes and Development (2005) 19(18):2122-37.

Capriolo et al., "Nucleic Acids: Overview and analytical strategies in: Mass Spectrometry in Biomolecular sciences." Kluwer Academic Publishers (1996) pp. 351-379.

Carothers et al., "Point Mutation Analysis in a Mammalian Gene: Rapid Preparation of Total RNA, PCR Amplification of CDNA, and Tag Sequencing by a Novel method" Biotechniques (1989) 7(5):494-499.

Chan et al., "Luminescent Quantum Dots for Mutilplexed Biological Detection and Imaging," Current Opinion in Biotechnology (2002) 13:40-46.

Cone et al., "Coamplified Positive Control Detects Inhibition of Polymerase Chain Reactions," J Clin Microbiol (1992) 30(12):3185-3189.

Crofts et al., "Multiple promoters direct the tissue-specific expression of novel N-terminal variant human vitamin D receptor gene transcripts," Proc Natl Acad Sci USA (1998) 95:10529-10534.

Cross, "Detection of BCR-ABL in hematological malignancies by RT-PCR," Methods in Molecular Medicine, Molecular Diagnosis of Cancer (1996) pp. 25-36.

Dingle et al., "Stable and noncompetitive RNA internal control for routine clinical diagnostic reverse transcription-PCR," J Clin Microbiol (2004) 42:1003-1011.

Dunnen et al., "Current Protocols in Human Genetics," (2006) 9(3):1-22.

Ehmer et al., "Variation of Hepatic Glucuronidation: Novel Functional Polymorphisms of the UDP-Glucuronosyltransferase UGT1A4," Hepatology (2004) 39(4):970-977.

Fitch et al., "Analysis of transcriptional isoforms of collagen types IX, II, and I in the developing avian cornea by competitive polymerase chain reaction," Developmental Dynamics (1995) 202(1):42-53.

Fredriksson et al., "Multiplex amplification of all coding sequences within 10 cancer genes by Gene-Collector," Nucleic Acids Research (2007) 35(7):e47.

Gao et al., "In Vivo Molecular and Cellular Imaging With Quantum Dots" Current Opinion in Biotechnology (2005) 16:63-72.

Gonzalez et al., "Multiple displacement amplification as a pre-polymerase chain reaction (pre-PCR) to process difficult to amplify samples and low copy number sequences from natural environments," Environ Microbiol (2005) 7(7):1024-1028.

Hayes et al., "Dual analyte immunoassay for proteins using releasable metal ions as labels (Albumin, immunoglobulin G)," Dissertation Abstracts International (1992) 53(9B):4624.

He et al., "Alternative splicing of the multidrug resistance protein 1/ATP binding cassette transporter subfamily gene in ovarian cancer creates functional splice variants and is associated with increased expression of the splicing factors PTB and SRp20," Clin. Cancer Research (2004) 10(14):4652-4660.

Horton, "Optimized Conditions for Cycle Sequencing of PCR Products" PCR Methods and Applications (1994) 3:359-360.

Hui et al., "Identification of mutations in seven Chinese patients with x-linked chronic granulomatous disease," Blood (1996) 88(10):4021-4028.

Innis et al., "PCR Protocols. A guide to Methods and Applications," Academic Press (1989) pp. 39-45.

International Search Report for PCT/CA2007/002333, dated Aug. 25, 2008, 4 pages.

Jacobsen et al., "Applications of mass spectrometry to DNA sequencing," GATA (1991) 8(8):223-229.

Johnson et al., "Genome-wide survey of human alternative pre-mRNA splicing with exon junction microarrays," Science (2003) 302(5653):2141-2144.

Jones et al., "Octamer-primed cycle sequencing using dye-terminator chemistry" Nucleic Acids Research (1998) 26(11):2824-2426.

Kapranov et al., "Examples of the complex architecture of the human transcriptome revealed by RACE and high-density tiling arrays," Genome Research (2005) 15(7):987-997.

Kotera et al., "Characterization and effects of methyl2-(4-aminophenyl)-1, 2-dihydro-1-oxo-7-(2-pyridinylmethoxy)-4-(3,4,5-trimethoxyphenyl)-3-isoquinoline carboxylate sulfate (T-1032), a novel potent inhibitor of cGMP-binding cGMP-specific phosphodiesterase (PDE5)," Biochem.Pharmacol (2000) 1:60(9):1331-1341.

Kretz et al., "Cycle Sequencing PCR Methods & Applications," Cold Spring Harbor Laboratory Press (1994) 3(5):S107-S112.

Li et al., "Direct electrophoretic detection of the allelic states of single DNA molecules in human sperm by using the polymerase chain reaction" Proc. Natl. Acad. Sci USA (1990) 87:4580-4584.

Maniatis et al., "Molecular Cloning, A Laboratory Manual" McGraw-Hill (1982) pp. 133, 134 and 143.

Marechal et al., "(CFTR) gene by denaturing high-performance liquid chromatography (D-HPLC): major im Complete and rapid scanning of the cystic fibrosis transmembrane conductance regulator applications for genetics counselling," Hum Genet (2001)108(4):290-298.

Martin et al., "Human angiotensin II type 1 receptor isoforms encoded by messenger. RNA splice variants are functionally distinct," Mol. Endocrinol (2001) 15(2):281-293.

Murray, "Improved Double-Stranded DNA Sequencing Using the Linear Polymerase Chain Reaction," Vincent Nucleic Acids Research (1989) 17(21): 8889.

(56) References Cited

OTHER PUBLICATIONS

Non Final Office Action for U.S. Pat. No. 6,197,510, dated Nov. 26, 1999.
Orban et al., "Expression profiles of BRCA1 splice variants in asynchronous and in G1/S synchronized tumor cell lines," Biochemical and Biophysical Research Communications (2001) 280(1):32-38.
Ozkan, "Quantum Dots and Other Nanoparticles: What Can They Offer to Drug Discovery," Drug Discovery Today (2004) 9(24):1065-1071.
Polymicrobial Disease Conference Chart: Identification of West Nile and Other Flaviviruses Using Multiplex Sequencing (MultiGEN), Oct. 19-23, 2003, Lake Tahoe.
Rawn, "Biochemistry" Carolina Biological Supply (1989) pp. 666, 708.
Ray et al., "Single cell multiplex PCR amplification of five dystrophin gene exons combined with gender determination," Molecular Human Reproduction (2001) 7(5):489-494.
Reiter et al., "Human Meiotic Recombination Products Revealed by Sequencing a Hotspot for Homologous Strand Exchange in Multiple HNPP Deletion Patients," Am. J. Hum. Genet. (1998) 62:1023-1033.
Roemer et al., "Simultaneous Bi-Directional Cycle Sequencing," LI-COR Virtual Poster Session [on-line], Sep. 1997, retrieved on Sep. 4, 1998, from Internet.
Roth et al., "Feasibility and efficacy of routine PCR screening of blood donations for hepatitis C virus, hepatitis B virus, and HIV-1 in a blood-bank setting," Lancet (1999) 353(9150):359-363.
Salerno et al., "Covalent modification with concomitant inactivation of the CAMP dependent protein kinase by affinity labels containing only 1-amino acids," J. biol. Chem. (1993) 268(18):13043-13049.
Sandhu et al., "Dual asymmetric PCR: one-step construction of synthetic genes," BioTechnics (1992) 12(1):14-16.
Sanger et al., "DNA Sequencing with Chain-Terminating Inhibitors" Proc Nat Acad Sci USA (1977) 74(12):5463-5467.
Schmittgen et al., "Expression of prostate specific membrane antigen and three alternatively spliced variants of PSMA in prostate cancer patients," Int J Cancer (2003) 1:107(2):323-9.
Shen et al., "Cycle Sequencing Using Degenerate Primers Containing Inosines," Biotechniques (1993) 15(1):82, 84, 88-89.
Shigemori et al., "Multiplex PCR: use of heat-stable Thermus thermophilus RecA protein to minimize non-specific PCR products," Nucleic Acids Research (2005) 33(14):e126.
Sloop et al., "Synthesis of 3-(triethylstannyl) propanioc acid: an organotin mass label for DNA," Bioconjugate Chemistry (1993) 4:406-409.
Spurgeon et al., "The Use of a Modified Taq DNA Polymerase for Thermal Cycle Sequencing of Double Strand Plasmid DNA Templates," Human Genome II. Int'l Conference (1990) San Diego, CA.
Steffens et al., "Multiplex Amplification of Human STR Loci using Infrared Fluorescence Detection," LI-COR Virtual Poster Session [on-line] (1997).
Sullivan et al., "Identification of human remains by amplification and automated sequencing of mitochondrial DNA," Int J Ieg Med (1992) 105:83-86.
Surono et al. "Circular Dystrophin RNAs Consisting of Exons That Were Skipped by Alternative Splicing," Human Molecular Genetics (1999) 8(3):493-500.
Van Doornum et al., "Diagnosing herpes virus infections by real time amplification and rapid culture," J Clin Microbiol (2003) 41:576-580.
Van Rooijen et al., "Structural Requirements of Oleosin Domains for Subcellular Targeting to the Oil Body," Plant Physiol (1995) 109:1353-1361.
Verdin et al., "Use of an internal control in a nested-PCR assay for Mycoplasma hyopneumoniae detection and quantification in tracheobronchiolar washings from pigs," Molecular and Cellular Probes (2000) 14:365-372.
Vinayagamoorthy et al., "24 hour urine composition of Sri Lankan adults and their response to 100mg dihydrochlorothiazide," Ann Clin Biochem (1980) 17(4):212-213.
Vinayagamoorthy et al., "A rapid non-selective method to generate quadromas by microelectrofusion," J Immunol Methods (1995) 187(1):1-7.
Vinayagamoorthy et al., "cDNA-based functional domains of a calnexin-like melanosomal protein," Melanoma Res (1993) 3(4):263-269.
Vinayagamoorthy et al., "Characterization of melanosome-associated proteins by establishment of monoclonal antibodies and immunoscreening of a melanoma cDNA library through an anti-melanosome antibody," Melanoma Res. (1993) 3(5):331-336.
Vinayagamoorthy et al., "Identification of a cDNA coding for a Ca(2+)-binding phosphoprotein (p90), calnexin, on melanosomes in normal and malignant human melanocytes," Exp Cell Res (1993) 209(2):288-300.
Vinayagamoorthy et al., Identification of Food Pathogens Using Multiple Nucleotide Based Signature Sequences. Presentation apart of PS 6C: Biotechnology Applications. Friday, Jul. 18, 2003.
Vinayagamoorthy et al., "Identification of the Severe Acute Respiratory Syndrome Coronavirus by Simultaneous Multigene DNA Sequencing," J Clin Microbiol (2004) 42(7):3291-3294.
Vinayagamoorthy et al., "Incidence of pGS01 and pGSO4 type sulphonamide resistance genes among clinical isolates collected from hospitals in Sri Lanka," Singapore Med J. (1986) 27(4):312-316.
Vinayagamoorthy et al., "Mobilization of antibiotic resistance genes among farm animals and human hosts in a developing country (Sri Lanka)," Singapore Medical Journal (1987) 28(2):134-139.
Vinayagamoorthy et al., "Molecular cloning, sequencing, and analysis of the cDNA for rabbit muscle glycogen debranching enzyme," Archives of Biochemistry and Biophysics (1993) 306(1):232-239.
Vinayagamoorthy et al., "Molecular control of melanogenesis in malignant melanoma: functional assessment of tyrosinase and lamp gene families by UV exposure and gene co-transfection, and cloning of a cDNA encoding calnexin, a possible melanogenesis "chaperone"," J Dermatol (1994) 21(11):894-906.
Vinayagamoorthy et al., "Molecular Typing of West Nile Virus, Dengue, and St. Louis Encephalitis Using Multiplex Sequencing," Journal of Molecular Diagnostics (2005) 7(2):152-159.
Vinayagamoorthy et al., "Novel type of plasmid-borne resistance to trimethoprim," Antimicrob Agents Chemother (1987) 31(1):60-66.
Vinayagamoorthy et al., "Nucleotide sequence based multi-target identification," J Clin Microbiol (2003) 41(7):3284-3292.
Vinayagamoorthy et al., "Rational Drug Design Based on Splice Variants," GEN (2004) 24(9):20-21.
Vinayagamoorthy et al., "R-plasmid-mediated antibiotic resistance genes among clinical isolates, "normal healthy" adults and a drinking water source in a developing country," Asian Medical Journal (1986) 29(1):50-68.
Vinayagamoorthy et al., "Simultaneous genotyping of sexually transmitted bacterial pathogens using MultiGEN technology," International Society for Sexually Transmitted Diseases Research, Conference (2003) Jul. 27-30, Ottawa, Canada.
Vinayagamoorthy et al., "Stress Relief Protein Modulation by Calnexin," Annals of the New York Academy of Sciences (1996) 793:479-484.
Vinayagamoorthy, "Detection of Giardia Lamblia and Cryptosporidium Parvum in Water Samples Using Multiplex Sequencing Technology," American Laboratory (2004) 36(10):46-50.
Vinayagamoorthy, "DNA Sequence-Based High-Throughput Microbial Identification Using Multiplex Sequencing," American Biotechnology Laboratory (2003).
Vinayagamoorthy, et al., "Identifying MRSA with Multiplex Sequencing," GEN (2008) 28(6):1-3.
Visible Genetics, Inc., Application Note, HiV Genotyping using the OpenGene Automated DNA Sequencing System, Jan. 16, 1998.
Visible Genetics, Inc., Application Note, p53 Mutation Detection using the OpenGene Automated DNA Sequencing System, May 3, 1998.

(56) References Cited

OTHER PUBLICATIONS

Voss et al., "Automated Cycle Sequencing with Taquenase TM: Protocols for Internal Labeling, Dye Primer and "DoubleX" Simultaneous Sequencing," Biotechnics (1997) 23(2):312318.

West et al., "Engineered Nanomaterials for Biophotonic Applications: Improving Sensing, Imaging, and Therapeutics," Annual Review of Biomedical Engineering (2003) 5:285-292.

Wharton et al., "Antiproliferative effects of phosphodiesterase type 5 inhibition in human pulmonary artery cells," Care Med (2005) 172(1)1:05-113.

White et al., "Concatemer Chain Reaction: A Tag DNA Polymerase-Mediated Mechanism for Generating Long Tandemly Repetitive DNA Sequences," Anal Biochem (1991) 199(2):184-190.

Wistow et al., "Expressed sequence tag analysis of human retina for the NEIBank Project: retbindin, an abundant, novel retinal cDNA and alternative splicing of other retina-preferred gene transcripts," Molecular Vision (2002) 15:8:196-204.

Yang et al., "Hypersensitive PCR, ancient human mtDNA, and contamination," Human Biology (2003) 75:355-364.

Ye et al., "Gene synthesis and expression in *E.coli* for PMP, a human matrix metalloproteinase," Biochemical and Biophysical Research Communications (1992) 186(1):143-149.

Yamakawa, Hisashi et al., "A DNA Cycle Sequencing Reaction that Minimizes Compressions on Automated Fluorescent Sequencers", *Nucleic Acid Research*, 25:6, pp. 1311-1312 (1997).

```
                          SEQUENCE LISTING

<160> NUMBER OF SEQ ID NOS: 16

<210> SEQ ID NO 1
<211> LENGTH: 18
<212> TYPE: DNA
<213> ORGANISM: Artificial Sequence
<220> FEATURE:
<223> OTHER INFORMATION: Synthetic primer

<400> SEQUENCE: 1
gggacacttt ggttcggg                                                     18

<210> SEQ ID NO 2
<211> LENGTH: 16
<212> TYPE: DNA
<213> ORGANISM: Artificial Sequence
<220> FEATURE:
<223> OTHER INFORMATION: Synthetic primer

<400> SEQUENCE: 2
tgggacggca aggggg                                                       16

<210> SEQ ID NO 3
<211> LENGTH: 20
<212> TYPE: DNA
<213> ORGANISM: Artificial Sequence
<220> FEATURE:
<223> OTHER INFORMATION: synthetic primer

<400> SEQUENCE: 3
atcttgttga gggcagggga                                                   20

<210> SEQ ID NO 4
<211> LENGTH: 21
<212> TYPE: DNA
<213> ORGANISM: Artificial Sequence
<220> FEATURE:
<223> OTHER INFORMATION: Synthetic primer

<400> SEQUENCE: 4
ggataagatg ctgaggaggg g                                                 21

<210> SEQ ID NO 5
<211> LENGTH: 21
<212> TYPE: DNA
<213> ORGANISM: Artificial Sequence
<220> FEATURE:
<223> OTHER INFORMATION: synthetic primer

<400> SEQUENCE: 5
ttgcgtgtgg agtatttgga t                                                 21

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
ttatggcggg aggtagactg a                                                 21
```

```
<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7
attctcagaa gcagctatca g                                          21

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
caggccatga tggtgttgta g                                          21

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
accaattact tctccgagga c                                          21

<210> SEQ ID NO 10
<211> LENGTH: 21
<212> TYPE: DNA
<213> ORGANISM: Artificial Sequence
<220> FEATURE:
<223> OTHER INFORMATION: Synthetic primer

<400> SEQUENCE: 10
gaagatgaca aatcccgaaa c                                          21

<210> SEQ ID NO 11
<211> LENGTH: 21
<212> TYPE: DNA
<213> ORGANISM: Artificial Sequence
<220> FEATURE:
<223> OTHER INFORMATION: Synthetic primer

<400> SEQUENCE: 11
acacagcatt caagcggatg t                                          21

<210> SEQ ID NO 12
<211> LENGTH: 18
<212> TYPE: DNA
<213> ORGANISM: Artificial Sequence
<220> FEATURE:
<223> OTHER INFORMATION: Synthetic primer

<400> SEQUENCE: 12
gaggtggcca aagacgca                                              18

<210> SEQ ID NO 13
<211> LENGTH: 25
<212> TYPE: DNA
<213> ORGANISM: Artificial Sequence
<220> FEATURE:
<223> OTHER INFORMATION: Synthetic Primer
```

```
<400> SEQUENCE: 13
tgttgtccta cccaaataag actca                                               25

<210> SEQ ID NO 14
<211> LENGTH: 25
<212> TYPE: DNA
<213> ORGANISM: Artificial Sequence
<220> FEATURE:
<223> OTHER INFORMATION: Synthetic Primer

<400> SEQUENCE: 14
gagcttctgt gcatcatagt atcca                                               25

<210> SEQ ID NO 15
<211> LENGTH: 26
<212> TYPE: DNA
<213> ORGANISM: Artificial Sequence
<220> FEATURE:
<223> OTHER INFORMATION: Synthetic Primer

<400> SEQUENCE: 15
atccacagga aatgaagaca tacagt                                              26

<210> SEQ ID NO 16
<211> LENGTH: 27
<212> TYPE: DNA
<213> ORGANISM: Artificial Sequence
<220> FEATURE:
<223> OTHER INFORMATION: Synthetic Primer

<400> SEQUENCE: 16
ataccacaca aattcaatac ggattct                                             27
```

DETERMINATION OF VARIANTS PRODUCED UPON REPLICATION OR TRANSCRIPTION OF NUCLEIC ACID SEQUENCES

CROSS-REFERENCE TO RELATED APPLICATION

This application is a continuation of U.S. patent application Ser. No. 11/475,921 filed Jun. 28, 2006 which will issue as U.S. Pat. No. 9,150,906 on Oct. 6, 2015. The content of this application is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 717482000201SeqList.txt, date recorded: Jan. 19, 2016, size: 3,398 bytes).

BACKGROUND OF THE INVENTION

1. Field of the Invention

This invention relates to means for determining variants of an expected nucleic acid sequence in the population formed when a substrate nucleic acid sequence is replicated, transcribed, edited, or transformed in similar ways. More particularly, the invention relates to the determination of the formation of expected sequences or variants upon such transformations to establish a better understanding and utilization of the role of such variants in genetic processes.

2. Background Art

All life forms have specific genomes that are based either on DNA or RNA (referred to collectively herein as nucleic acids). During cell processing, nucleic acids derived from the genome or other sources are frequently and routinely copied (replicated), transcribed, edited (in the case of eukaryotic organisms), and eventually translated into proteins. During such processing, there is normally an "expected" nucleic acid sequence that results from "normal" replication, transcription or editing, but frequently one or more variants of the expected sequence are formed either in addition to the expected sequence or in place of it. The formation of such variants can result from "errors" in the replication, transcription or editing processes, or may possibly result from normal cell processes, e.g. when genes overlap.

Knowledge of the formation of one or more variants of an expected sequence when nucleic acid transformations take place can provide useful information for scientists in various fields. For example, the formation of sequence variants may be indicative of disease in a particular individual or may help to explain a particular cellular process.

For example, in higher life forms (based on eukaryotic cells), including humans, the primary RNA transcript formed directly from a genetic DNA sequence undergoes editing by the cell before it is used as a template for protein formation (translation). During this process, non-coding regions of the gene (introns) are removed and coding regions (exons) are spliced together to form a functional mRNA template used for protein synthesis. Often, in nature, this editing process leads to the formation of different versions of mRNA (often referred to as "splice variants"). These different versions or variants may differ in the number and/or order of the exons incorporated into the mRNA, as well as the variation of nucleotides across the junction or splice points of adjacent exons.

It is estimated that more than 70% of gene expression events encounter splice variations, thus resulting in variations in expressed proteins, which undermines the established concept that one gene leads to only one version of the protein. The presence or level of specific splice variants may be the cause or an indicator of a disease, disorder, pathological condition or normal condition. Understanding the distribution of splice variants in various tissues is extremely important for understanding the physiological function of genes and for targeting pharmaceuticals in drug discovery, drug evaluation, as well as for diagnostic purposes.

The formation of variants in this way is not limited to the translation of DNA to mRNA in eukaryotic cells. Even in prokaryotic cells (where there are no introns and thus no editing of RNA transcripts), there may be minor variations (mutations) in some of the transcripts. Moreover, during cell division in both prokaryotic and eukaryotic cells, DNA to DNA copies are made, involving a number of enzymes (e.g RNA primase, DNA polymerase, exonuclease, ligase, etc.). Although these steps have built-in proof-reading mechanisms, such replication may result in variations in the copies of DNA formed leading to various abnormalities or diseases (Ref. 1, see References at the end of this disclosure).

A common way of determining the transcription products of cells of a tissue is to employ a DNA micro-array (often called a "gene chip"). In this method, short probes (each representing a gene) are printed on and secured to a slide or chip. The cDNA of the tested tissue, fluorescently labeled, is hybridized to the micro-array. The level of the resulting signal corresponds to the relative expression level of the associated nucleic segment in the population. However, such micro-arrays do not account for the variants among the population formed that carry such nucleic acid segments. Hence it is not the presence or absence of a nucleic acid segment that is important, but to determine and characterize the nucleic sequence species that carry those segments, e.g. if there is a nucleic segment (for example, an exon) that determines a drug binding site on the resultant protein, it is essential to know whether that exon is carried by a specific mRNA so that there will be proper folding of the protein resulting in specific protein structure conducive for binding of the drug.

In the recent past, computational modeling has been adopted as an alternative method for predicting protein structure, which is based on the amino acid sequences (primary structures) of proteins. Technical limitations of determining an amino acid sequence directly from the protein have made it necessary to predict the amino acid sequence from the nucleotide sequence of the mRNA template. The existence of splice variants formed during gene expression interferes with such predictions and has created two main problems for accurate prediction of protein structures; (a) exon composition in various mRNA transcripts formed (b) errors in splicing itself at the exon/exon junction of mRNA templates.

Presently, there is no method available to accurately determine all of the different transcripts that may be simultaneously expressed from a gene.

A method of determining all the sequence variants resulting from nucleic acid transformations would therefore be of practical significance.

SUMMARY OF THE INVENTION

An exemplary embodiment of the present invention provides a method of determining whether or not a nucleic acid having an expected sequence or one or more variant nucleic acids having a variant of the expected sequence is or are present in a sample containing nucleic acids after replication, transcription or editing of a substrate nucleic acid, which method comprises: deciding an expected sequence likely to be formed in the sample upon the replication, transcription or editing of the substrate nucleic acid, and possible variants of the expected sequence; providing at least one primer pair for a nucleic acid amplification step (e.g. polymerase chain reaction, reverse transcriptase polymerase chain reaction or ligase chain reaction), carrying out the amplification step to form one or more amplicons, and analyzing the one or more amplicons to determining whether or not a nucleic acid having the expected sequence or one or more variants is or are present in the sample, wherein primers of the at least one primer pair are designed to anneal to regions of the nucleic acid of the expected sequence and the one or more variant nucleic acid sequences, the regions being selected to reveal unambiguously the presence or absence in the sample of the nucleic acid of the expected sequence or the one or more variants thereof according to the presence or absence of amplicons amplified by the primers.

In most cases, the nucleic acid of expected sequence is known or can be readily determined, e.g. the sequence of DNA produced by replication (the sequence of the replicated DNA should be the same as the substrate DNA), or the mRNA transcribed from a known gene. Also, it is normally relatively easy to determine expected or suspected variants. For example, when exons of a gene are converted to mRNA, it can be expected that one or more of the exons may be missing, or the exons are aligned in a different order than the one expected. Further, when DNA containing a region of interest (e.g. a putative drug binding site in an eventual protein) is replicated or transcribed, a replicate or transcript lacking the region of interest may be suspected. The invention may be employed when there is an expected sequence and at least one expected or suspected variant of interest that may be formed. Primer sets can then be designed to reveal the presence or absence of such expected sequence and variant(s) in an unambiguous way (according to amplicons amplified by the primer sets) all in one PCR or RT-PCR procedure or in a sequence of two or more such procedures. Once the presence of at least one variant has been established in this way, the precise sequence of a region of interest (e.g. an exon:exon junction or a putative drug binding site) may be established, if desired, by cycle sequencing of such a region.

Procedures for designing and producing primers that anneal to short stretches of a known sequence are an integral part of the PCR and RT-PCR procedures and within the expected skill of persons knowledgeable in the art. When the substrate sequence is known, or at least the part that is relevant to the determination, the design of the primers involves identifying a suitable short stretch of the known sequence where amplification should begin and end, thereby generating suitable amplicons that give an unambiguous indication of the sample sequence, and creating a short stretch of complementary DNA that will anneal to the selected stretch of the sample DNA. Ideally, one primer set is designed for each of the expected sequence and all of the possible variants of interest, there being at least one variant of interest as well as the expected sequence.

Another exemplary embodiment of the invention provides a method of determining whether or not a nucleic acid having an expected sequence is present in a sample after linking together of at least two nucleic acid sequence units capable of forming the nucleic acid of the expected sequence, and whether at least one nucleic acid having a variants of the expected sequence is formed, which method comprises providing at least one pair of polymerase chain reaction primers designed to amplify a region of the nucleic acid of the expected sequence, the region crossing at least one junction between adjacent sequence units of the expected sequence, carrying out polymerase chain reaction or reverse transcriptase polymerase chain reaction on the sample employing the primers to permit amplification of the region, thereby forming an amplification product, carrying out an analysis of the amplification product to establish sizes of one or more amplicons present in the amplification product, and using information from the analysis to determine if a nucleic acid of the expected sequence was present in the sample and if one or more nucleic acids having variants of the expected sequence was or were formed during the linking together of the sequence units by omission of one or more of the sequence units or by variation of an expected order of assembly of the sequence units.

Yet another exemplary embodiment of the invention provides a method of determining a presence or absence of variants in a sample produced during the formation of nucleic acids upon linking of a plurality of known sequence units, which method comprises: providing a plurality of primer pairs adapted to amplify specific nucleic acid sequences during polymerase chain reactions or reverse transcriptase polymerase chain reaction, each of the plurality of primer pairs being designed to amplify partial sequences of two of the known sequence units, there being sufficient primer pairs of different design to provide amplified sequences containing partial sequences of all the known sequence units; carrying out polymerase chain reaction or reverse transcriptase polymerase chain reaction on the sample using the plurality of primer pairs simultaneously to produce a reaction mixture containing amplified nucleic acids of different lengths; establishing the lengths of the amplified nucleic acids; and determining the variants present in the sample based the lengths of the amplified nucleic acids.

A still further exemplary embodiment of the invention provides a method of determining an exact sequence of bases adjacent to a junction of two nucleic acid sequence units in a sample nucleic acid formed by linking of the sequence units, thereby to establish a presence or absence of variants of an expected sequence at the junction, which method comprises isolating and amplifying a region of the sample nucleic acid crossing the junction and including bases on each side of the junction, and subjecting the isolated region to cycle sequencing to determine an exact sequence of bases thereof.

In the context of the present invention, the term "sequence unit" means any nucleic acid sequence that is manipulated as a whole during the formation of a new nucleic acid sequence, e.g. by splicing together two or more such units obtained from a precursor sequence, such as a eukaryotic gene sequence. Thus, the exons of a eukaryotic gene are examples of sequence units when they are transcribed to RNA and spliced together to form mRNA during protein synthesis. It is when such units are joined, linked or spliced by natural or artificial processes that splice variants may be formed, e.g. by loss of one or more entire units, misalignment of the units compared to the expected alignment, and variation of bases at the junction of the units.

Also, as used herein, the term polymerase chain reaction (PCR) may include reverse transcription polymerase chain reaction (RT-PCR) carried out on an mRNA substrate, when the context makes this apparent.

The term "amplicon" as used herein means a molecule or collection of molecules (population) obtained by amplifying a particular nucleic acid sequence by PCR or RT-PCR.

Potential splice variant targets that may be investigated by the methods of the present invention include (but are not limited to) the following:
1. Soluble proteins:
   a. Lipitor® (Anticholesterol drug) target protein-3-hydroxy-3-methylglutaryl-coenzyme A (HMG-CoA)
   b. Viagra®-Phosphodiesterase type 5 (PDE 5)
      Splice variant has been reported (Ref. 2)
2. Membrane proteins:
   a. Prostrate cancer receptor—Prostrate specific membrane antigen
      Splice variant has been reported (Ref. 3)
   b. Human Angiotension II type receptor
      Splice variant has been reported (Ref. 4)
   c. ATP-binding cassette transporter A1, ABCA1
      Splice variant has been reported (Ref. 5)
   d. Human Usher syndrome harmonin
      Splice variant has been reported (Ref. 6)
   e. HIV receptors CD 46, CD 4, CD 8
   f. The human constitutive androstane receptor (hCAR; NR1I3
      Splice variant has been reported
   g. Serum response factor (SRF)
      Splice variant has been reported
   h. Sodium-Proton pump receptors
      Splice variant has been reported.
3. House-keeping proteins:
   a. p53 suppressor protein
      Splice variant has been reported
   b. Heat shock protein hsp 70-House keeping gene.

DETAILED DESCRIPTION OF THE PREFERRED EMBODIMENTS

Figure 1:
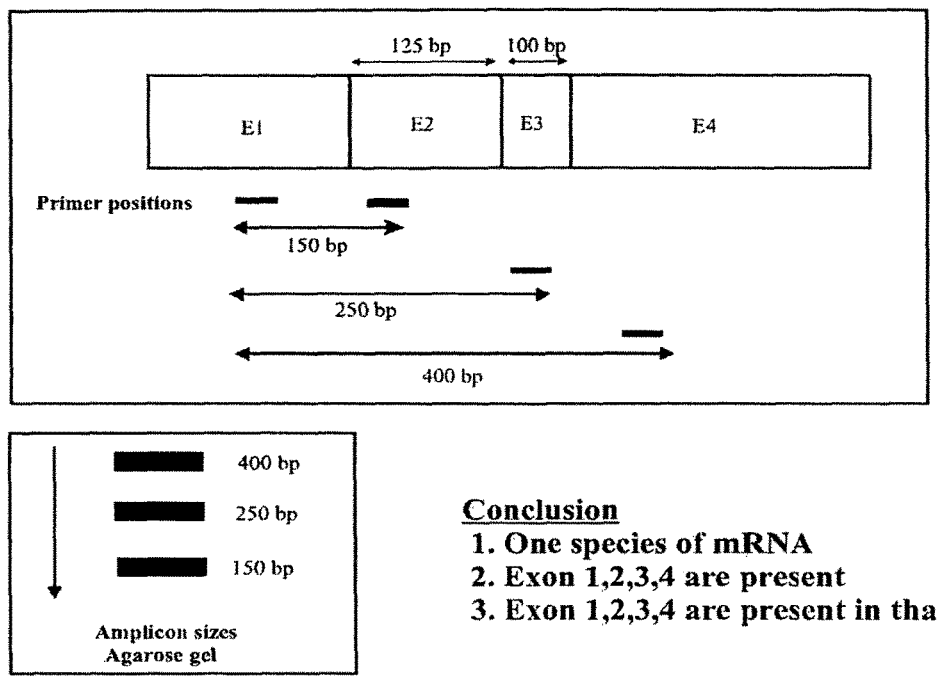
FIGS. 1 to 3 are diagrams illustrating one preferred form of the present invention as it relates to the detection of splice variants.

The present invention may be employed in various situations involving nucleic acid replication, transcription, editing, or other such nucleic acid transformations. However, the invention will first be illustrated as it relates to a situation in which nucleic acid sequences containing two or more specific known (or partially known) nucleic acid sequence units are spliced together or copied during a natural or artificial process and where variations may occur during the splicing or copying procedure. Specifically, the description refers to the translation and editing of genetic DNA containing exons as the specific sequence units, as well as non-coding introns, but it will be appreciated from comments above that this is not the only situation in which the present invention may be employed.

The invention makes use of the polymerase chain reaction (PCR) to amplify short sections of DNA, or reverse transcription PCR (RT-PCR) to amplify complementary DNA (cDNA) from sequences of mRNA (e.g. messenger RNA or mRNA). PCR and RT-PCR are well-known processes that involve well-established techniques described, for example, in Molecular Cloning: A Laboratory Manual, by Sambrook and Russel, $3^{rd}$ Edition, Cold Spring Harbor Laboratory Press, 2001 (the disclosure of which is incorporated herein by reference). PCR and RT-PCR are very similar, except that reverse transcriptase is used in RT-PCR to initially form cDNA from sample RNA extract, and then the cDNA is subjected to amplification by PCR. In the PCR and RT-PCR procedures, use is made of pairs of primers (upstream, "up" or forward primers, and downstream, "down" or reverse primers), which are short stretches of nucleic acids having sequences designed to anneal to known base sequences of a double-stranded substrate molecule. The primers form the start and stop positions for the sequence replication, so the sequence between (and incorporating) the primers is amplified during the PCR cycles.

In the present invention, primer pairs are designed to cause the amplification of sequences crossing (bracketing) regions of interest where sequence variants may occur. In the context of exon splicing, the regions of interest are the possible junctions between nucleic acid sequence units (exons). Essentially, all possible splice variants (as well as the expected sequence) are worked out in advance so that the expected and possible order in which the exons may be joined is known. Primers are then designed to anneal to parts of the various sequences to reveal (in terms of the amplicons that they produce during PCR) the presence (or absence) of the expected sequence or any variants. This means designing primers that amplify sequences crossing one or more possible splices between exons. The results of PCR or RT-PCR using such primers, e.g. the existence and size of corresponding amplicons, can then be used as information to determine the sequences present in the sample material. Preferably, sufficient primer pairs are designed and provided (either in one PCR procedure, or in several procedures carried out sequentially) to produce amplicons from the expected sequence and all possible splice variants. This can best be illustrated by the following examples in which reference is made to the accompanying drawings.

The bar at the top of FIG. 1 represents an mRNA molecule made up of four exons (RNA sequences) spliced together, i.e. exons E1, E2, E3 and E4. It should be appreciated that, in this example, the number of exons and base pairs shown in the drawing are chosen just for illustration purposes only and that, in real situations, other numbers and lengths may apply. In a simple case, three primer pairs are provided, each having a common upstream primer P1 designed to anneal to a sequence present only in exon E1. Three downstream primers, P2, P3 and P4 are designed to anneal to specific sequences within each of E2, E3 and E4, respectively. When these primers are present during RT-PCR all at the same time, and when the sample mRNA has the exons spliced in the order E1, E2, E3 and E4 as shown, three DNA sequences will be amplified by the RT-PCR procedure. Thus, the primer pair P1:P2 will amplify a 150 base pair (bp) region crossing the E1:E2 splice as shown, primer pair P1:P3 will amplify a 250 bp region crossing the E1:E2 and E2:E3 splices as shown, and primer pair P1:P4 will amplify a 400 bp region crossing the E1:E2, E2:E3 and E3:E4 splices. The presence of these amplicons in the amplification product mixture, and their approximate lengths, can be detected by conventional means, e.g. agarose gel electrophoresis used conventionally to separate amplified DNA products resulting from the PCR procedure. In this case, the electrophoresis will show three bands corresponding to sequences of 150, 250 and 400 bases, as expected (as represented by the lane shown in the lower left hand corner of FIG. 1). This result leads to the conclusion that there is only one specie of mRNA molecule, i.e. that exons E1, E2, E3 and E4 are present, and that the exons are arranged in the expected order.

Figure 2:
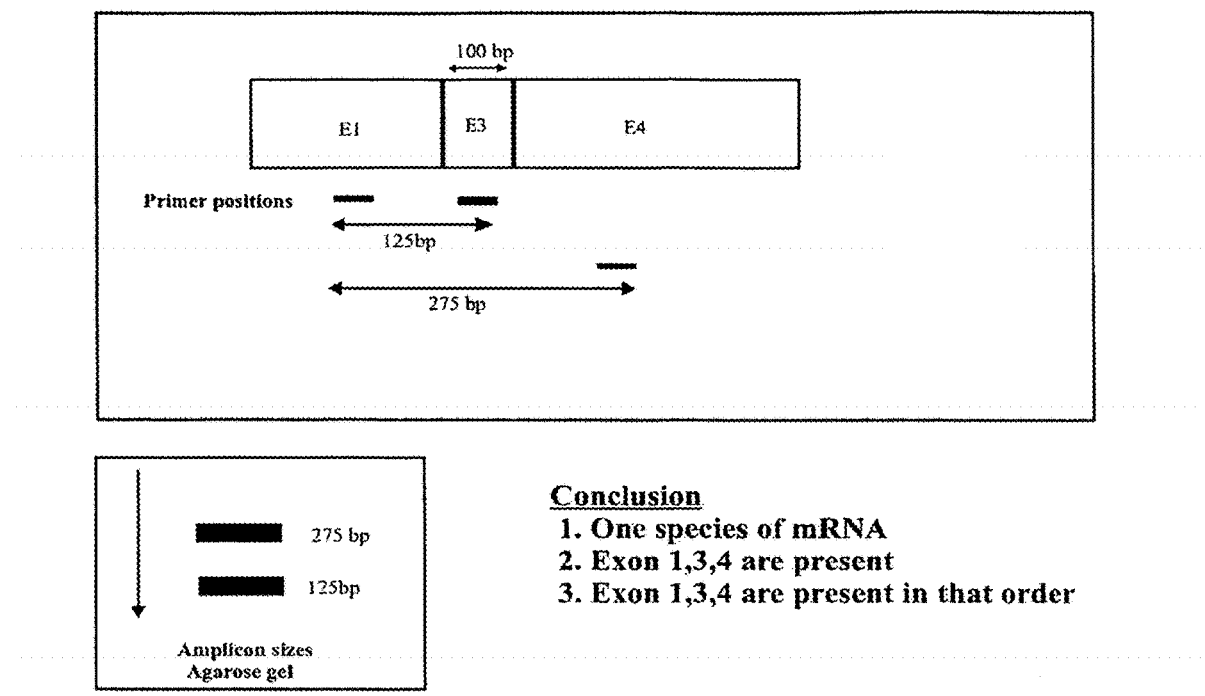

FIG. 2 shows an alternative molecule of mRNA from which exon E2 is absent compared to the sequence of FIG. 1. In this case, downstream primer P2 will not bind to the sample sequence, but downstream primers P3 and P4 will bind as before. However, as E2 has a length of 125 bases (as shown in FIG. 1), but is now absent, the primer pair P1:P3 will now amplify a sequence of 125 bases, and the primer pair P1:P4 will now amplify a sequence of only 275 bases. In such a case, the gel electrophoresis will show two bands corresponding to these amplified sections and the appearance of two such bands will lead to the conclusion that there is only one specie of mRNA present in the sample and that the sample contains exons E1, E3 and E4 arranged in the stated order.

Figure 3:
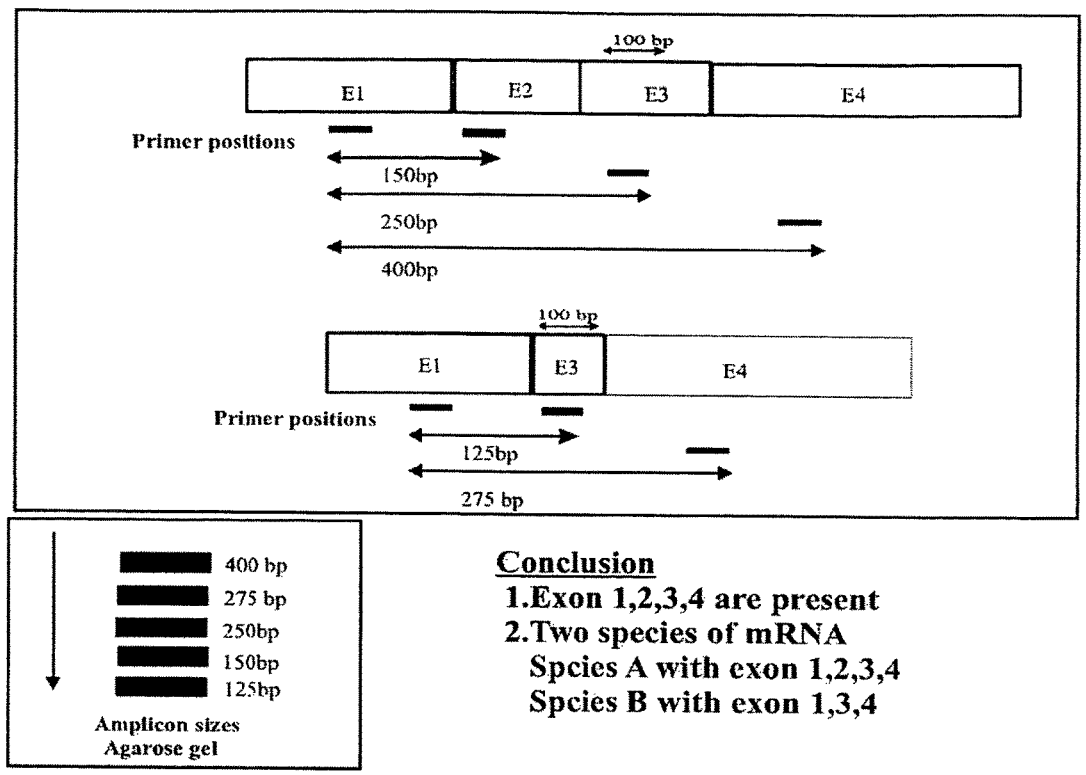

FIG. 3 illustrates a situation in which there are two species of mRNA molecule, i.e. a specie containing E1, E2, E3 and E4 arranged in that order, and a specie consisting only of exons E1, E3 and E4. The first specie will give the results of FIG. 1, i.e. amplification of three sequences of 150, 250 and 400 bp. In the case of the second specie, the result will be the same as in FIG. 2, i.e. the amplification of two sequences of 125 and 275 bp. The combined result will therefore show bands for 5 amplified sequences of 125, 150, 250 275 and 400 bp, as shown in FIG. 3. Therefore, such a result will signify the presence of two variants, one with exons E1, E2, E3 and E4 arranged in the stated order, and the other with only exons E1, E3 and E4 arranged in the stated order.

Therefore, by providing an upstream primer corresponding to a sequence of an exon likely (a) to be in the first position in any variant, and (b) likely to be present in all variants, as well as downstream primers corresponding to a sequences from all other exons likely to be present, the amplification results can be analyzed to determine (1) how many species of mRNA are present, and (2) the number and order of exons in each mRNA variant. The process works for at least three exons and corresponding primers, and may be carried out for any number of exons, provided the resulting sequences can all be amplified by PCR or RT-PCR. Normally, there are 2 to 20 exons present in a functional gene transcript. To avoid ambiguous results, the primers should preferably be designed to produce amplified sequences of different lengths in all cases (the differences of length being sufficient to produce different discernable bands in gel electrophoresis), and the lengths of the exons should be known (as well as at least a part of their sequence so that primers may be designed).

While the above example requires exon E1 to be present in all variants, as well as E1 being the first exon in any likely sequence, if an amplicon is to be obtained, the invention is not limited to such cases. This was necessary only because all of the primers pairs of that example use a common upstream primer P1 that anneals to a section of the sequence of E1. It is possible instead to provide primer pairs having different upstream primers as well as different downstream primers, the primers being designed to amplify sequences that will cross all possible exon-exon splices. Ideally, the upstream primer of each exon is positioned towards the 3'-end of the exon sequence, and the downstream primer is positioned on or close to the 5'-end. For a sequence having six exons E1 to E6 arranged in that order, there would be 15 amplified PCR products, i.e. as shown in Table 1 below:

TABLE 1

| 1 | E1 up | + | E6 down |
|---|---|---|---|
| 2 | E1 up | + | E5 down |
| 3 | E1 up | + | E4 down |
| 4 | E1 up | + | E3 down |
| 5 | E1 up | + | E2 down |
| 6 | E2 up | + | E6 down |
| 7 | E2 up | + | E5 down |
| 8 | E2 up | + | E4 down |
| 9 | E2 up | + | E3 down |
| 10 | E3 up | + | E6 down |
| 11 | E3 up | + | E5 down |
| 12 | E3 up | + | E4 down |
| 13 | E4 up | + | E6 down |
| 14 | E4 up | + | E5 down |
| 15 | E5 up | + | E6 down |

These amplicons may be formed in a single PCR reaction using all primer pairs at once, or alternatively, in more than one reaction using different combinations of primer pairs (in the extreme, one primer pair is provided for each PCR reaction). The presence of the stated 15 amplicons indicates that all exons are present and that the order is as expected. However, if (for example) E3 is missing, the amplicons will be as shown in Table 2 below:

TABLE 2

| 1 | E1 up | + | E6 down |
|---|---|---|---|
| 2 | E1 up | + | E5 down |
| 3 | E1 up | + | E4 down |
| 4 | E1 up | + | E2 down |
| 5 | E2 up | + | E6 down |
| 6 | E2 up | + | E5 down |
| 7 | E2 up | + | E4 down |
| 8 | E4 up | + | E6 down |
| 9 | E4 up | + | E5 down |
| 10 | E5 up | + | E6 down |

This means that there will be only ten amplicons, and the amplicons that would otherwise have spanned E3 (amplicons 1, 2, 3, 5, 6 and 7) will be reduced in size by number of base pairs in E3. If the number of base pairs in E3 is known, this will indicated that it is E3 that is missing.

On the other hand, if all six exons are present, but the order follows E2, E1, E3, E4, E5 and E6, the following amplicons will be detected, as shown in Table 3 below:

TABLE 3

| 1 | E2 up | + | E6 down |
|---|---|---|---|
| 2 | E2 up | + | E5 down |
| 3 | E2 up | + | E4 down |
| 4 | E2 up | + | E3 down |
| 5 | E2 up | + | E2 down |
| 6 | E1 up | + | E6 down |
| 7 | E1 up | + | E5 down |
| 8 | E1 up | + | E4 down |
| 9 | E1 up | + | E3 down |
| 10 | E3 up | + | E6 down |
| 11 | E3 up | + | E5 down |
| 12 | E3 up | + | E4 down |
| 13 | E4 up | + | E6 down |
| 14 | E4 up | + | E5 down |
| 15 | E5 up | + | E6 down |

Thus, there will still be 15 amplicons, but the amplicons involving E1 and E2 will be of a different length than those of the first case above (provided E1 and E2 differ in size and/or binding position of the respective primers). This difference of length will be characteristic of the positioning of the exons in the stated re-arranged order.

An alternative approach uses different primer pairs sequentially. For example, if a primer pair is designed with an upstream primer on E1 and a downstream primer on E6, the following amplicons will be produced if E1 and E6 are present at the ends but the other exons are either present or absent, as shown in Table 4 below:

TABLE 4

| Exons | Full mRNA | | | | | | # Exons | Amplicon Size |
|---|---|---|---|---|---|---|---|---|
| | E6 | E5 | E4 | E3 | E2 | E1 | | |
| | | | Length (bp) | | | | | |
| | 111 | 143 | 164 | 104 | 200 | 135 | | |
| | PCR fragment length | | | | | | | |
| All present | 111 | 143 | 164 | 104 | 200 | 135 | 6 | 857 |
| E5 absent | 111 | | 164 | 104 | 200 | 135 | 5 | 714 |
| E4 absent | 111 | 143 | | 104 | 200 | 135 | 5 | 693 |
| E3 absent | 111 | 143 | 164 | | 200 | 135 | 5 | 753 |
| E2 absent | 111 | 143 | 164 | 104 | | 135 | 5 | 657 |
| E5&E4 absent | 111 | | | 104 | 200 | 135 | 4 | 550 |
| E5&E3 absent | 111 | | 164 | | 200 | 135 | 4 | 610 |
| E5&E2 absent | 111 | | 164 | 104 | | 135 | 4 | 514 |
| E4 & E3 absent | 111 | 143 | | | 200 | 135 | 4 | 589 |
| E4 & E2 absent | 111 | 143 | | 104 | | 135 | 4 | 493 |
| E2 & E3 absent | 111 | 143 | 164 | | | 135 | 4 | 553 |
| E5, E4 & E3 absent | 111 | | | | 200 | 135 | 3 | 446 |
| E5, E4 & E2 absent | 111 | | | 104 | | 135 | 3 | 350 |
| E5, E3 & E2 absent | 111 | | 164 | | | 135 | 3 | 410 |
| E5, E4, E3 & E2 absent | 111 | 143 | | | | 135 | 3 | 389 |
| E5, E4, E3 & E2 absent | 111 | | | | | 135 | 2 | 246 |

The presence or absence of such amplicons indicates the presence or absence of the corresponding exons.

Of course, in this case, if no amplicon whatsoever is produced, it can be assumed that either E1 or E6 (or both) is absent. Further PCR reactions can then be carried out sequentially or simultaneously with primer pairs E1/E5, E2/E6 or E2/E5. A lack of amplicon for one or more of these PCR reactions will show if E1, E6 or both E1 and E6 are missing, e.g. no amplicon from E1/E5 shows that E1 or E5 is missing, no amplicon from E2/E6 shows that E6 or E2 is missing, amplicon produced from E2/E5 confirms that E2 and E5 are present, so the failure to produce an amplicon in one or both of the other reactions means that E1 or E6 is missing.

Figure 4:
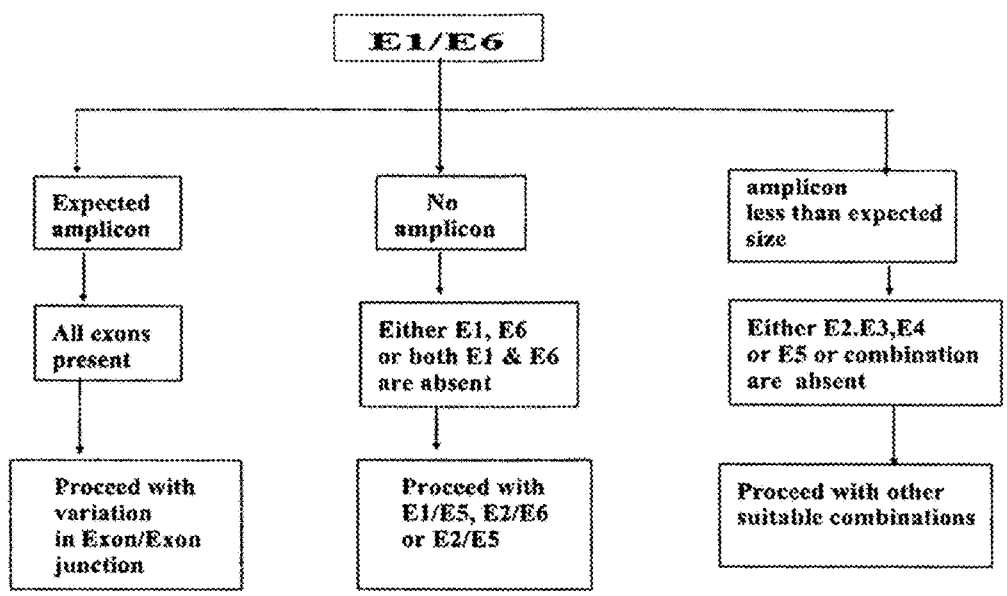
FIG. 4 is a diagram showing a variation of the methods of FIGS. 1 to 3.

This approach can be summarized as shown in FIG. 4 of the accompanying drawings. As represented, an RT-PCR reaction is first carried out with primers E1/E6, and the results will be either an amplicon of the expected size (all exons present in the expected order), in which case the investigation of the precise sequences at the exon-exon junctions may be commenced (see below), or alternatively, no amplicon is produced (which indicates that E1 or E6, or both, are absent and this can be investigated using further RT-PCR with different primer pairs (e.g. E1/E5, E2/E6 and E2/E5 primers), or alternatively, an amplicon of shorter length is detected (which indicates that one of E2, E3, E4 and E5, or a combination of these exons, is missing, in which case further investigation may be carried out with other primer pairs, e.g. E1/E3, etc.).

While the invention is particularly suitable for use with sequences of at least 3 exons, it is possible also to apply it to a sequence of only two exons. In this case, if a single primer pair E1/E2 is employed, an amplicon will either be produced or not. The formation of an amplicon will show that both E1 and E2 are present. The absence of an amplicon will indicate either that E1 or E2 is absent, or that they are reversed (E2:E1). The latter can then be identified by using a primer pair E2/E1.

It should be mentioned that the above procedure may be carried out using the ligase chain reaction as an alternative to PCR and RT-PCR. Ligation is process by which two single stranded nucleotide sequences are joined 3'-prime end to 5'-prime end after both have annealed to a common single-stranded sequence. The joining will only take place across a single nucleotide gap. This may be used to detect the order of exons as well as nucleotide variations across exon/exon junctions.

Figure 5:
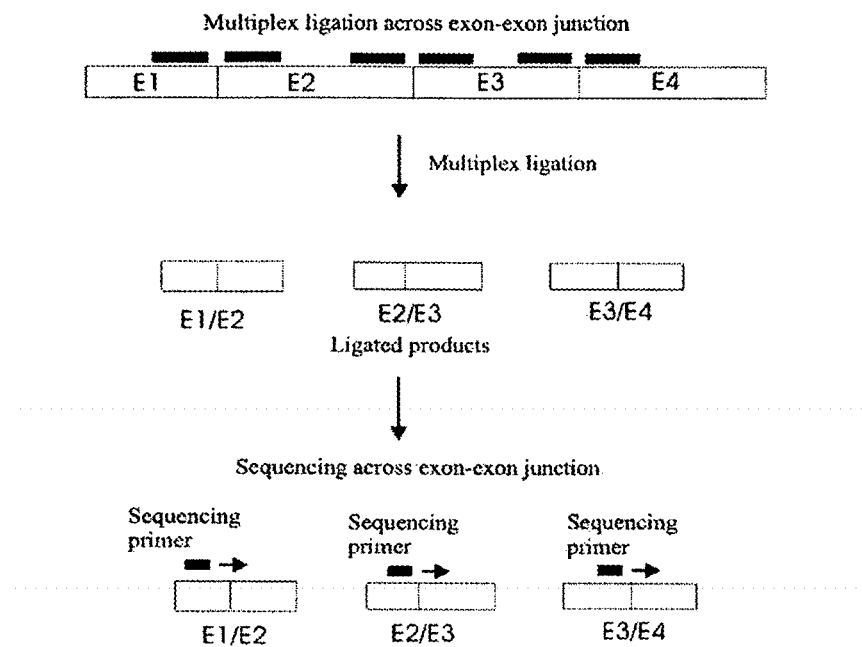
FIG. 5 is a diagram showing an alternative procedure using ligase chain reaction.

The procedure involves designing primers to bracket exon-exon junctions, carrying out conventional multiplex ligation and then sequencing across exon-exon junctions of the resulting amplicons. This is illustrated in FIG. 5 of the accompanying drawings.

Other Sequence Determinations

As noted above, the present invention is particularly suitable for the detection of splice variants, i.e. when known sequence units are spliced together. However, the invention may also be applied to other circumstances, as illustrated in FIG. 6.

Figure 6:
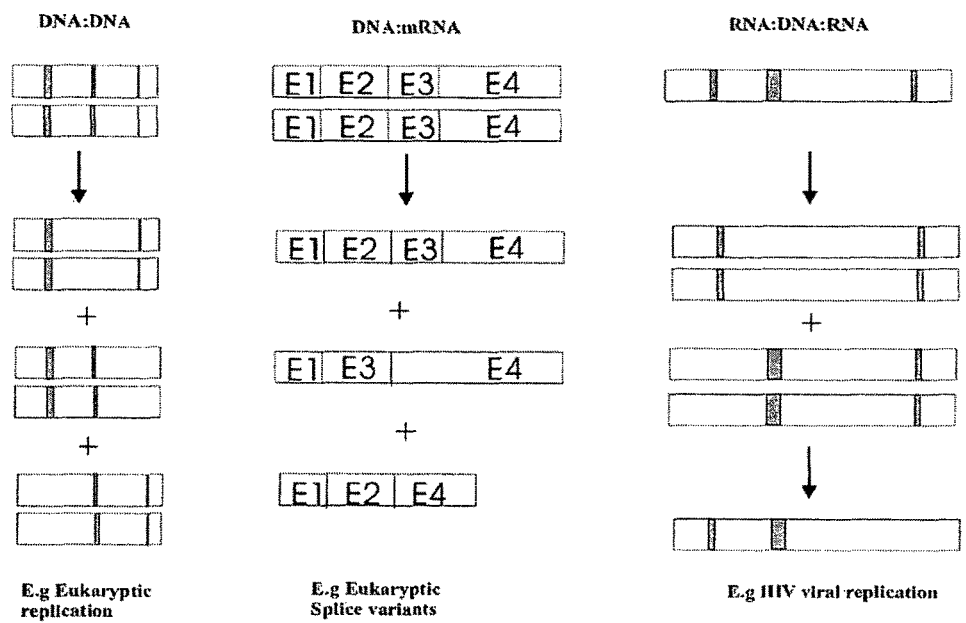
FIG. 6 is a diagram showing alternative transformations to which the present invention may be applied.

In FIG. 6, the left hand column illustrates DNA to DNA replication that takes place, for example, during the processes of eukaryotic cells. The box pair at the top represent DNA containing three "markers" shown in grey (i.e. sequences of interest to a researcher, such as sequences that may indicate a genetic disease, a single nucleotide polymorphism—SNP, or a possible binding site for a drug, or a modification that affects protein folding). During replication, as well as an expected sequence containing all three markers positioned identically to the substrate DNA, there are possible variants, e.g. as shown in the three box pairs beneath the arrow (which represents replication). In the three variants shown, one of the three markers is missing, but a different one in each case. There could, of course, be additional variants with two or all of the markers missing, but this may be statistically less-likely. In such a case, the present invention may be operated by designing primers to amplify sequences crossing the markers and analyzing the resulting amplicons by sequencing. Hence, the amplicons reveal the variants present.

The central column of FIG. 6 illustrates the splicing of exons as already described in detail above.

The right hand column in FIG. 6 illustrates conversion of RNA to DNA and then further conversion of DNA to RNA. Such conversions are typical of RNA viral replication in cells, e.g. the HIV virus. As illustrated, the viral RNA may contain three markers of interest. This RNA is converted to DNA as shown by the arrow but, in addition to the expected sequence containing all three markers, two variants are shown each having one of the markers missing. When the DNA is inserted into the genome of a host and the DNA is transcribed to RNA, the RNA may lack the third marker as shown. The presence or absence of the markers in the final RNA may be determined by carrying out RT-PCR using primers designed to bracket each of the marker sequences, as in the case described for the left hand column. The resulting amplicons can thus reveal the presence or absence of the marker sequences of interest.

It will therefore be seen that the present invention, in one broad form, applies when a nucleic acid transformation takes place from a sequence containing two or more sequences or sequence units of interest and the transformation may result in the formation of variants that lack one or more of the sequences or sequence units of interest or contain such sequences or sequence units in re-arranged order. By designing primers targeted to produce amplicons that reveal the presence of such sequences or sequence units, or such differences in order thereof, the presence (or absence) of the expected sequence or one or more variants may be revealed.

Detection of Variants that Differ By a Small Number of Bases

The above procedure identifies missing or mis-arranged sequences of interest, e.g. exons, but it may not be sufficiently precise to reveal variants that differ by only a few base pairs, e.g. minor deletions at exon-exon junctions, because gel electrophoresis designed for separation of molecules of significant size differences may not discernibly separate molecules that differ only by a few bases (e.g. 1 to 25 bases). If such sequence variations are of interest (which is often the case, because such variations also affect protein folding when translated), a further process of the invention may be employed to determine the formation of such variants. This method is preferably carried out after the above procedure, i.e. after the presence of variants incorporating larger sequences segments of interest, have been determined.

Using the splicing of exons as an example, essentially, in this method, a section of an amplicon extending across an exon-exon junction of interest is isolated and then subjected to cycle sequencing to establish the exact sequence of bases in the region of the junction. However, since cycle sequencing may be carried out on only short sequences, the method involves isolating for such sequencing a short section including the part where small variations may occur (e.g. at the exon-exon junctions).

Cycle sequencing is a known procedure that is employed to determine the exact sequence of bases within a short stretch of DNA (see for example, Hisashi Yamakawa and Osamu Ohara, "A DNA Cycle Sequencing Reaction that Minimizes Compressions on Automated Fluorescent Sequencers", Nucleic Acid Research, Vol. 25, No. 6, pp. 1131-1312, the disclosure of which is incorporated herein by reference). In chain terminator sequencing (Sanger sequencing), extension is initiated at a specific site on the template DNA by using a short oligonucleotide 'primer' complementary to the template at that region. The oligonucleotide primer is extended using a DNA polymerase, an enzyme that replicates DNA. Included with the primer and DNA polymerase are the four deoxynucleotide bases (DNA building blocks), along with a low concentration of a chain terminating nucleotide (most commonly a di-deoxynucleotide). Limited incorporation of the chain terminating nucleotide by the DNA polymerase results in a series of related DNA fragments that are terminated only at positions where that particular nucleotide is used. The fragments are then size-separated by electrophoresis in a slab polyacrylamide gel, or more commonly, in a narrow glass tube (capillary) filled with a viscous polymer (Pop 7; Applied Biosystems, USA). Each sample has a primer of the four normal deoxynucleotides (dATP, dGTP, dCTP and dTTP), DNA polymerase, and all four of the dideoxynucleotides (ddATP, ddGTP, ddCTP and ddTTP) added to it in the same tube. The dideoxynucleotides are added in limited quantities. The primer or the dideoxynucleotides has a fluorescent tag. As the DNA strand is elongated the DNA polymerase catalyses the joining of deoxynucleotides to the corresponding bases. However, if a di-deoxynucleotide is joined to a base, then that fragment of DNA can no longer be elongated since a dideoxynucleotide lacks a crucial 3'-OH group. Fragments of all sizes should be obtained due to the randomness of when a dideoxynucleotide is added. However, to make sure that all different lengths will occur, only short stretches (less than about 800 bases) of DNA can be sequenced in one test. The DNA is then denatured and the resulting fragments are separated (with a resolution of just one nucleotide) by gel electrophoresis, from longest to shortest. Amplicons were sequenced by cycle sequencing using ABI PRISM Big Dye Terminator Cycle Sequencing Ready Reaction Kit (Applied Biosystems, USA) on a GeneAmp 2400 thermocycler (PE Applied Biosystems, USA) using thermocycler. Unincorporated dye terminators were removed using Centricep chromatography columns (Princeton, USA). The samples were then dried, and re-suspended in 20 ul of ABI PRISM Template Suppression Reagent(TSR). Samples were analyzed by capillary electrophoresis using the ABI PRISM Genetic Analyzer 310. The 47 cm×50 um uncoated capillary was filled with a Performance Optimized Polymer 6 (acrylamide/urea polymer) and heated to 500° C. 20 ul of the sequencing mixture was pipetted into a 0.2 mL microfuge tube provided by the manufacturer (Applied Biosystems, USA). Samples were drawn into the capillary by electrokinetic injection at 2 Kv for 50 to 200 seconds. The electrophoresis was carried out at 15 Kv for 20 minutes Preferred cycle sequencing procedures are illustrated in the following with reference to FIGS. 5, 7 and 8.

Figure 7:
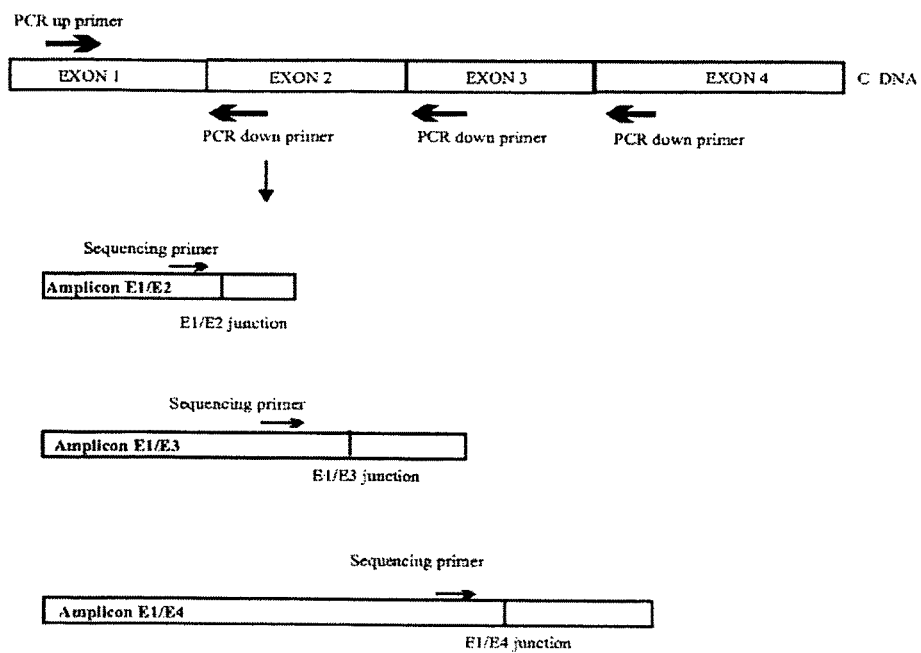
FIGS. 7 and 8 are diagrams illustrating other preferred forms of the invention as it relates to the determination of precise sequences at the junctions of adjacent nucleic acid sequence units.

FIG. 7 represents a procedure similar to that of FIG. 1 using PCR downstream primers that anneal close to or at the exon junctions E1:E2, E2:E3, E3:E4, which thereby produce amplicons having 3'-ends spanning and terminating close to the junctions. The resulting amplicons (after being used confirming the presence of the exons and the order of alignment) can be used for cycle sequencing.

Figure 8:
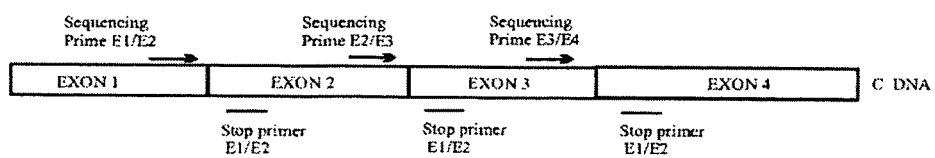

FIG. 8 shows the use of stop primers designed to terminate sequencing at a position more than a few bases on the downstream sides of the junctions of several exons on an amplicon that spans several exons. Sequencing primers designed to anneal just a few bases upstream of the junctions are also used for sequencing.

Essentially, one of three methods may be employed.

(1) Assuming that a peptide nucleic acid (PNA) stop primer method can be implemented, the following steps may be carried out.

(i) PNA primers are designed that will bind to each exon approximately 10 to 15 base pairs on the 3' side of the exon-exon junction.

(ii) The sample DNA is denatured and PNA primers added, and they are allowed to anneal to the sample DNA.

(iii) A dye terminator is added (e.g. Big Dye Terminator® v3.1 of Applied Biosystem, USA), sequencing primers are added and cycle sequence performed.

(iv) Sequencing is carried out preferably on a capillary gel sequencer or a flat gel electrophoresis to establish the exact sequence of the isolated DNA section.

PNA is an artificially synthesized chemical similar to DNA or RNA but differing in the composition of its "backbone" which comprises repeating N-(2-aminoethyl)-glycine units linked by peptide bonds. The various purine and pyrimidine bases are linked to the backbone by methylene carbonyl bonds. Since the backbone of PNA contains no charged phosphate groups, the binding between PNA/DNA strands is stronger than between DNA/DNA strands due to the lack of electrostatic repulsion. PNA thus stops further DNA replication during PCR and hence can be used to tailor amplicons to match regions of interst.

(2) Assuming Stoffel conditions (PCR without 5'-3' exonuclease activity) and that stop primers work.

(i) Design stop primers that will bind to each exon approximately 10-15 bp on the 3' side of the junction.

(ii) Create single-stranded DNA (ssDNA) using PCR technology and only one primer.

(iii) Add the stop primers and allow them to anneal.

(iv) Add the dye terminator mixture (e.g. BDT v3.1; Applied Biosystems, USA) and the sequencing primers and sequenced in a thermocycler.

Stoffel conditions allow the use of the so-called "Stoffel fragment" for PCR. This is a modified form of AmpliTaq® DNA polymerase from which the N-terminal 289 amino acids have been deleted. The Stoffel fragment differs from AmpliTaq® DNA polymerase in that it is more thermostable (by approximately two-fold), exhibits optimal activity over a broader range of magnesium ion concentration (2 mM-10 mM) and lacks intrinsic 5' to 3' exonuclease activity. The unique properties of the Stoffel fragment make it especially useful for arbitrarily primed PCR (AP-PCR) or random amplified polymorphic DNA (RAPD) amplification methods, whereby genomic DNA is amplified with a set of short primers of arbitrary sequence.

(3) Carry out a series of PCRs to generate short amplicons from the entire gene sequence, e.g. exons 1-2, 2-3, 3-4 and 4-5 (in individual tubes)

(i) Design primers that are 15-20 bp on the 5' side of the 3' end of the downstream primer for each exon.

(ii) The amplicons are then pooled for 1 cycle sequencing reaction.

The presence or absence of a sequence (expected sequence or variant sequence) will indicate which primer sets are required for additional PCR reactions and cycle sequencing steps.

1. Digest the fragments with restriction enzymes so that every exon is cleaved into two pieces.

2. A sequencing primer can then be used to sequence each exon-exon junction to determine which exon is absent or nucleotide variation at the splicing junction.

The invention is illustrated in further detail by reference to the following Examples which are not intended to limit the scope of the present invention.

EXAMPLE 1

Summary

Three gene expressions were analyzed, namely: prostrate specific membrane antigen (PSMA) in PC3 cell lines, tumor suppressor protein (p53) and (HTT) in SW480 and hepatoma cell lines. It was found that PSMA had one splice variant, PSMAV1, lacking exon 19. However, PSMAV1 exhibited nucleotide sequence variations at the exon18/exon20 junction. There were no splice variants observed for p53 tumor suppressor gene in these three cell lines. However, gene expression in SW480 and hepatoma cells had nucleotide variations between the exon8/exon9 junctions.

Materials and Methods

Cell Cultures

Cell cultures of Vero E6 cells were obtained from the University of Saskatchewan. These cells were grown in RPMI medium supplemented with 5% fetal calf serum in a 50 ml culture.

Total RNA extraction

Total RNA was extracted using the RNeasy® Mini Kit (Qiagen, USA). The reagents of the kit were prepared according to the manufacturer's instructions and 350 µL of RLT buffer and 250 µL of 100% ethanol were added to 100 µL of viral lysate. The sample was transferred to a spin column and centrifuged at 8,000 rcf for 30 seconds. The sample was washed on the spin column three times, once with 700 µL RW1 buffer and twice with 500 µL RPE buffer. After each wash the spin column was centrifuged at 8,000 rcf for 30 seconds. After washing, the column was thoroughly dried with a 1-minute centrifugation at 8,000 rcf. Finally, the sample was eluted from the column by adding 50 µL RNase-free water to the column and centrifuging for 1 minute at 8,000 rcf. The RNA was further concentrated by re-applying the eluate to the column and centrifuging a second time at 8,000 rcf for 1 minute.

RT-PCR

The SuperScript® One-Step RT-PCR with Platinum Taq kit (Invitrogen, USA) was used for individual RT-PCR. The reaction volume was 50 µL which consisted of 25 µL 2× Reaction mix, 200 nM of each primer, 1 µL RT/Platinum mix Taq and 50 ng of West Nile Virus RNA. The tubes were placed in a thermocycler, GeneAmp® 2400 (Applied Biosystems, USA) and amplified according to the thermocycling profile shown in Table 1.

Gel Electrophoresis

The amplicons were visualized by loading 2 µL 6× loading buffer, 5 µL TBE buffer and 5 µL of the PCR product onto a 2% agarose gel and applying 110V for 50 minutes. The gel was then stained for 15 minutes in ethidium bromide (5 µg/ml) TBE solution and then destained in distilled water for 15 minutes.

Cycle Sequencing

Amplicons were sequenced by cycle sequencing using ABI PRISM Big Dye Terminator® Cycle Sequencing Ready Reaction Kit (Applied Biosystems, USA) on a GeneAmp 2400 thermocycler (PE Applied Biosystems, USA) using thermocycler profile on Table 1. Unincorporated dye terminators were removed using Centricep® chromatography columns (Princeton, USA). The samples were then dried, and re-suspended in 20 µl of ABI PRISM Template Suppression Reagent. Samples were analyzed by capillary electrophoresis using the ABI PRISM Genetic Analyzer 310. The 47 cm×50 um uncoated capillary was filled with a Performance Optimized Polymer® 6 (acrylamide/urea polymer) and heated to 50° C. 20 µl of the sequencing mixture was pipetted into a 0.2 mL microfuge tube provided by the manufacturer (Applied Biosystems, USA). Samples were drawn into the capillary by an electric current (electrokinetic injection) at 2 Kv for 50 to 200 seconds. The electrophoresis was carried out at 15 Kv for 20 minutes.

Results

Total RNA was extracted from PC3 prostrate cancer cell lines, SW480, HTT29 and human hepatoma cancer cells.

P53

RT-PCR with exon 1 up-primer and exon 6 down-primer produced expected band 677 bp. RT-PCR with exon 6 up-primer and exon 11 down-primer produced expected band 542 bp.

HTT

RT-PCR with HTT 1a and HTT 1b produced expected band 562 bp; HTT 2a and HTT 2b produced expected band 513 bp, HTT 3a and HTT 3b produced expected band 706 bp.

PSMA

RT-PCR with Exon4 up/exon 8 down produced expected band of 569 bp and Exon 17 up/exon 20 down produced expected band 441 bp and abnormal band of 341 bp. Sequencing whole amplicon (341 bp) confirmed that exon 19 is missing.

Based on the amplicon sizes it generated, PSMA showed two transcripts; a full length mRNA and an alternative splice variant without exon19; both p53 and HTT had only one transcript each. These amplicons were sequenced using upstream PCR primer. Transcript from PSMA showed nucleotide variations at exon18/exon20 junction to that of the reported results. Similarly, p53 showed nucleotide variations at exon8/exon9 junction.

The primers used in this Example are shown in Table 5 below:

TABLE 5

| Primers | | | |
|---|---|---|---|
| P53 | | | |
| P53 | 1exonup:466u18 | GGGACACTTTGGTTCGGG | (SEQ ID NO. 1) |
| P53 | down34exon:654L16 | TGGGACGGCAAGGGGG | (SEQ ID NO. 2) |
| P53 | down5exon:935L20 | ATCTTGTTGAGGGCAGGGGA | (SEQ ID NO. 3) |
| P53 | down6exon:112L21 | GGATAAGATGCTGAGGAGGGG | (SEQ ID NO. 4) |
| P53 | 6exonup:1157U21 | TTGCGTGTGGAGTATTTGGAT | (SEQ ID NO. 5) |
| P53 | down11exon:1678L21 | TTATGGCGGGAGGTAGACTGA | (SEQ ID NO. 6) |
| HTT | | | |
| HTT | Htt1a:130U21 | ATTCTCAGAAGCAGCTATCAG | (SEQ ID NO. 7) |
| HTT | Htt1b:635L21 | CAGGCCATGATGGTGTTGTAG | (SEQ ID NO. 8) |
| HTT | Htt2a:738U21 | ACCAATTACTTCTCCGAGGAC | (SEQ ID NO. 9) |
| HTT | Htt2b:1230L21 | GAAGATGACAAATCCCGAAAC | (SEQ ID NO. 10) |
| HTT | Htt3a:1981L21 | ACACAGCATTCAAGCGGATGT | (SEQ ID NO. 11) |
| HTT | Htt3b:1296U18 | GAGGTGGCCAAAGACGCA | (SEQ ID NO. 12) |
| PSMa | | | |
| PSM | e4psm:608U25 | TGTTGTCCTACCCAAATAAGACTCA | (SEQ ID NO. 13) |
| PSM | e8psm:1152L25 | GAGCTTCTGTGCATCATAGTATCCA | (SEQ ID NO. 14) |
| PSM | e17psm:2114U26 | ATCCACAGGAAATGAAGACATACAGT | (SEQ ID NO. 15) |
| PSM | e20psm:2528L27 | ATACCACACAAATTCAATACGGATTCT | (SEQ ID NO. 16) |

REFERENCES

1) Molecular Biology of the Cell, by Bruce Alberts et al, 1994 Garland Science publication).
2) Kotera J, Fujishige K, Michibata H, Yuasa K, Kubo A, Nakamura Y, Omori K., Biochem.Pharmacol. 2000 Nov. 1;60(9):1331-41, *Characterization and effects of methyl-2-(4-aminophenyl)-1,2-dihydro-1-oxo-7-(2-pyridinyl-methoxy)-4-(3,4,5-trimethoxyphenyl)-3-isoquinoline carboxylate sulfate (T-1032), a novel potent inhibitor of cGMP-binding cGMP-specific phosphodiesterase (PDE5).*
3) Schmittgen T D, Teske S, Vessella R L, True L D, Zakrajsek B A., Int J Cancer. 2003 Nov. 1; 107(2):323-9, *Expression of prostate specific membrane antigen and three alternatively spliced variants of PSMA in prostate cancer patients.*
4) Martin M M, Willardson B M, Burton G F, White C R, McLaughlin J N, Bray S M, Ogilvie J W Jr, Elton T S., Mol. Endocrinol. 2001 February;15(2):281-93, *Human angiotensin II type 1 receptor isoforms encoded by messenger RNA splice variants are functionally distinct.*
5) He X, Ee P L, Coon J S, Beck W T., Clin.Cancer Research. 2004, Jul. 15:10(14):4652-60, *Alternative splicing of the multidrug resistance protein 1/ATP binding cassette transporter subfamily gene in ovarian cancer creates functional splice variants and is associated with increased expression of the splicing factors PTB and SRp20.*

6) Wistow G, Bernstein S L, Wyatt M K, Ray S, Behal A, Touchman J W, Bouffard G, Smith D, Peterson K., Mol. Vis 2002 Jun. 15:8:196-204, *Expressed sequence tag analysis of human retina for the NEIBank Project: retbindin, an abundant, novel retinal cDNA and alternative splicing of other retina-preferred gene transcripts.*

The invention claimed is:

1. A method of determining whether or not a mRNA having an expected sequence or one or more variant mRNAs with a varying order of exons is or are present in a sample containing mRNAs after transcription or editing of a substrate mRNA which method comprises:

generation of an expected order of exons likely to be formed in said sample upon said transcription and/or variations of the expected order of the exons, editing of said substrate mRNA producing expected nucleotide sequences of the exons and/or variations of the expected nucleotide sequences of the exons, providing at least one downstream primer for reverse transcriptase, thereby producing a complementary DNA (cDNA), wherein the cDNA produced comprises more than one exon;

carrying out an amplification step to form an amplicon, wherein the amplification step utilizes forward and reverse primers, wherein the primers are designed to amplify a region of the cDNA and the region crosses at least one junction between adjacent exons of said cDNA; and analyzing the one or more amplicons, thereby determining whether or not a mRNA having said expected sequence, or the one or more variant mRNAs are present in said sample, wherein said regions being selected to reveal unambiguously the presence or absence in said sample of said mRNA having-said expected sequence or said one or more variant mRNAs thereof according to the presence or absence of amplicons amplified by said primers.

2. The method of claim 1 wherein said substrate-mRNA comprises at least three exons.

3. The method of claim 1, wherein, following said analyzing, the order of the exons of said mRNA is determined.

4. A method of determining whether or not a mRNA-having an expected sequence is present in a sample after linking together of at least two exons that form the expected mRNA sequence, and whether at least one mRNA having a variant or variants of said expected sequence is formed, which method comprises:

providing ligase chain reaction primers designed to produce a complementary DNA (cDNA) comprising a region, wherein said mRNA and cDNA comprise at least two exons and said region crosses at least one junction between adjacent exons of said mRNA carrying out ligase chain reaction using a pair of oligonucleotides to amplify said region, thereby forming an amplification product, carrying out an analysis of said amplification product to establish sizes of one or more amplicons present in said amplification product, and using information from said analysis to determine if an exon of said expected sequence is present in said sample and if one or more mRNAs having variants of said expected sequence was or were formed during said linking together of at least two said exons by omission of one or more of said exons or by variation of an expected order of assembly of said exons in said mRNAs.

5. The method of claim 1, wherein said expected mRNA sequence comprises two exons having an intervening exon/ exon junction, and pair of primers, each pair of at least two pairs of said forward and reverse primers, comprises one member that is an upstream forward primer designed to anneal to a first of said exons on an upstream side of said junction, and reverse primer designed to anneal to a second of said exons at or downstream of said junction.

6. The method of claim 1, wherein said expected mRNA sequence comprises three or more exons having intervening exon/exon junctions, and pair of forward and reverse primers, one member that is an upstream primer designed to anneal to a first one of said exons, and a reverse primer being a downstream primer designed to anneal to a final one of said exons.

* * * * *